(12) United States Patent
Slusher et al.

(10) Patent No.: US 8,778,688 B2
(45) Date of Patent: Jul. 15, 2014

(54) HIGH-THROUGHPUT METHODS FOR DETERMINING PHARMACOLOGICAL LEVELS OF PLASMA D-SERINE

(71) Applicant: The Johns Hopkins University, Baltimore, MD (US)

(72) Inventors: Barbara S. Slusher, Kingsville, MD (US); Jesse Alt, Essex, MD (US); Camilo Rojas, Baltimore, MD (US); Takashi Tsukamoto, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/672,102

(22) Filed: Nov. 8, 2012

(65) Prior Publication Data
US 2013/0116293 A1 May 9, 2013

Related U.S. Application Data

(60) Provisional application No. 61/556,900, filed on Nov. 8, 2011.

(51) Int. Cl.
*G01N 33/68* (2006.01)
*G01N 21/64* (2006.01)

(52) U.S. Cl.
USPC ............... 436/89; 436/63; 436/86; 436/161; 436/164; 436/172; 436/175; 436/178; 435/28

(58) Field of Classification Search
USPC ............ 436/63, 86, 89, 161, 164, 172, 174, 436/175, 177, 178; 422/69, 70, 82.08, 527; 435/28, 29
See application file for complete search history.

(56) References Cited

U.S. PATENT DOCUMENTS

2009/0306169 A1* 12/2009 Brandish et al. ............... 514/412
2010/0029737 A1* 2/2010 Heffernan et al. ............. 514/411
2010/0163432 A1* 7/2010 Marinesco et al. ............ 205/787

OTHER PUBLICATIONS

Alt et al. Analytical Biochemistry, vol. 419, Aug. 16, 2011, pp. 106-109.*
Brandish, et al., "A Cell-Based Ultra-High-Throughput Screening Assay for Identifying Inhibitors of D-Amino Acid Oxidase," J Biomol Screen 11:481-87 (2006).
Ferraris, et al., "Synthesis and Biological Evaluation of D-Amino Acid Oxidase Inhibitors," J Med Chem, 51:3357-59 (2008).
Fukushima, et al., "Simultaneous determination of D- and L-serine in rat brain microdialysis sample using a column-switching HPLC with fluorimetric detection," Biomed Chromatogr 18:813-19 (2004).
Hashimoto, A., "Determination of free amino acid enantiomers in rat brain and serum by high-performance liquid chromatography after derivatization with N-tert.-butyloxycarbonyl-Lcysteine and o-phthaldialdehyde," J Chromatography B, 582:41-48 (1992).
Hashimoto, et al., "Free D-serine, D-aspartate and D-alanine in central nervous system and serum in mutant mice lacking D-amino acid oxidase," Neuroscience Letters, 152:33-36 (1993).
Hashimoto, et al., "Co-Administration of a D-Amino Acid Oxidase Inhibitor Potentiates the Efficacy of D-Serine in Attenuating Prepulse Inhibition Deficits After Administration of Dizocilpine," Biol Psychiatry, 65:1103-6 (2009).
Smith, et al., "The Behavioral and Neurochemical Effects of a Novel D-Amino Acid Oxidase Inhibitor Compound 8 [4H-Thieno [3,2-b]pyrrole-5-carboxylic Acid] and D-Serine," J Pharmacol Exp Ther 328:921-30 (2009).

* cited by examiner

*Primary Examiner* — Maureen Wallenhorst
(74) *Attorney, Agent, or Firm* — Foley Hoag LLP

(57) ABSTRACT

Described herein are high-throughput methods of monitoring D-serine levels in plasma. The assay involves the use of strong cation solid phase extraction (SPE) to isolate D-serine from plasma, followed by quantitation of D-serine using the D-amino acid oxidase- (DAAO-) catalyzed reaction. Also described are methods of screening for compounds that act as DAAO inhibitors.

10 Claims, 4 Drawing Sheets

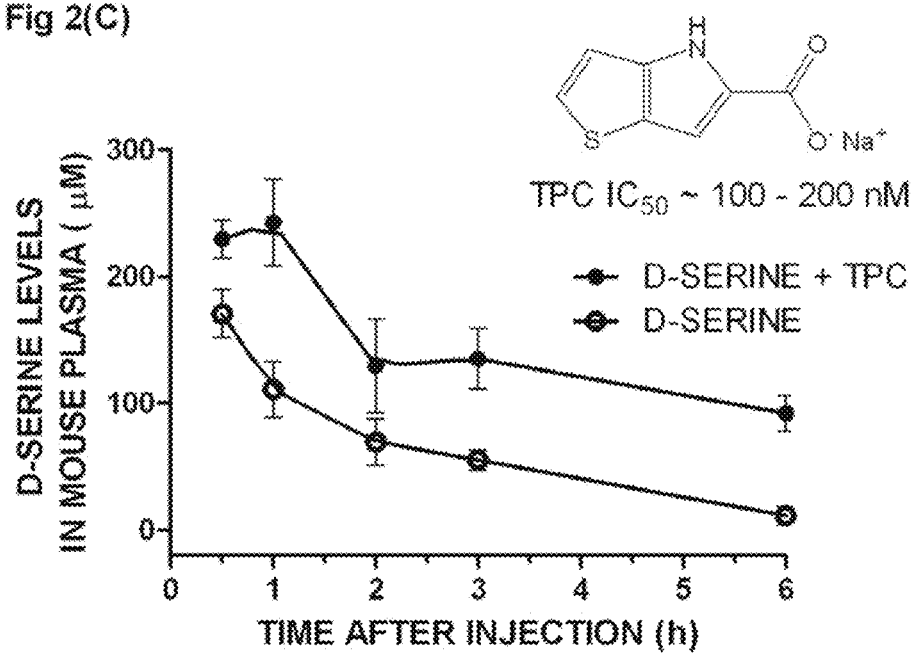

| Mobile Phase | pH of mobile phase | Measured pH of eluate | D-serine concentration (uM) |
|---|---|---|---|
| Flow Through | 1.5 | 1.5 | 0 |
| Rinse 1 | 1.5 | 1.5 | 0 |
| Rinse 2 | 1.5 | 1.5 | 0 |
| Eluent 1 | 8.5 | 2 | 0 |
| Eluent 2 | 8.5 | 2 | 0 |
| Eluent 3 | 8.5 | 2 | 0.6 |
| Eluent 4 | 13 | 7 | 13 |
| Eluent 5 | 13 | 9 | 29 |
| Eluent 6 | 13 | 12 | 0 |

HIGH-THROUGHPUT METHODS FOR DETERMINING PHARMACOLOGICAL LEVELS OF PLASMA D-SERINE

GOVERNMENT SUPPORT

This invention was made with Government support under Grant No. RO1 MH091387 awarded by the National Institutes of Health. The government has certain rights in this invention.

CROSS-REFERENCE TO RELATED APPLICATIONS

This application claims the benefit of U.S. Provisional Application No. 61/556,900, filed on Nov. 8, 2011; the contents of which application are specifically incorporated by reference.

BACKGROUND

D-serine is an endogenous allosteric activator of the N-methyl-D-aspartate (NMDA[1]) receptor. In multiple clinical studies, D-serine administration has been shown to be effective at treating the positive, negative and cognitive deficits of schizophrenia. In order to observe clinical effects, however, D-serine had to be administered at high doses (2 g per day po) multiple times per day (TID or BID). One reason for the high and frequent dose is that D-serine undergoes oxidation by D-amino acid oxidase (DAAO), a flavoenzyme expressed in the liver, kidney, and brain. Only a fraction of the administered D-serine is thought to cross the blood brain barrier and act on the presumed target, the NMDA receptor. One additional issue with D-serine therapy is that the products of D-serine oxidation, hydroxy pyruvate and hydrogen peroxide, have been associated with nephrotoxicity.

In order to address these problems, co-administration of D-serine with a DAAO inhibitor has been suggested to lower the dose of D-serine required to treat schizophrenia symptoms and also to prevent unwanted side effects caused by the DAAO-catalyzed reaction. Early results using this approach have been promising: oral co-administration of D-serine with a prototype DAAO inhibitor, 5-chloro-benzo[d]isoxazol-3-ol (CBIO), significantly enhanced plasma and brain levels of D-serine in rats compared to D-serine alone. D. Ferraris, et al. J Med Chem 51 (2008) 3357-59. Further, co-administration of CBIO with D-serine normalized prepulse inhibition deficits in ddy mice similar to the normalization observed when using 10-fold higher doses of D-serine alone. K. Hashimoto, et al. Biol Psychiatry 65 (2009) 1103-6. Drug-like DAAO inhibitors with acceptable pharmacokinetics and toxicity profiles are being sought as a novel therapeutic for patients with schizophrenia. In the early preclinical characterization of these new drug candidates inhibitors are evaluated in rodents for their ability to increase plasma D-serine levels after oral co-administration. Plasma D-serine could also be a useful pharmacodynamic marker to establish dose and a biomarker of drug effect once DAAO inhibitors are in the clinic.

Currently there are two HPLC-based methods to measure D-serine in plasma. One involves D-serine extraction, derivatization using N-tert-butyloxycarbonyl-L-cysteine and o-phthaldialdehyde followed by HPLC separation with a $C_{18}$ column and detection of fluorescent signal of derivatized D-serine. A. Hashimoto, et al. J Chromatogr 582 (1992) 41-48. The other method was originally implemented with rat brain microdialysis samples using two HPLC columns in tandem involving derivatization with 4-fluoro-7-nitro-2,1,3-benzoxadiazole (NBD-F), separation of the derivatized amino acids in an ODS column followed by a chiral column separation and fluorimetric detection. T. Fukushima, et al. Biomed Chromatogr 18 (2004) 813-19. Both methods allow for the separation of D-serine from other amino acids present in plasma including L-serine. These methods require 40-70 min chromatographic separations and are not amenable to concomitant analysis of multiple samples. Consequently, analyses of D-serine time profiles in plasma after co-administration with DAAO inhibitors is time consuming.

There exists a need for a high-throughput (e.g., a 96-well-format) assay to monitor D-serine in plasma.

SUMMARY

In certain embodiments, the invention relates to a method of quantifying D-serine in plasma comprising the steps of:
 (a) contacting a quantity of plasma with a quantity of a first acidic liquid, wherein the plasma comprises D-serine, thereby forming an acidified sample;
 (b) contacting the acidified sample with a quantity of a cation exchange resin, thereby separating the acidified sample into a first component and a second component, wherein the first component comprises D-serine and is retained on the resin;
 (c) rinsing the resin containing the retained first component with a quantity of a second acidic liquid;
 (d) contacting the resin with a quantity of a first basic liquid, thereby eluting from the resin D-serine and forming a D-serine eluent;
 (e) contacting the D-serine eluent with flavin adenine dinucleotide and a quantity of DAAO in the presence of Amplex Red and a quantity of horse radish peroxidase, thereby forming resorufin; and
 (f) detecting a fluorescence signal from resorufin.

In certain embodiments, the invention relates to a method of determining whether a compound is a DAAO inhibitor, comprising the steps of:
 (a) administering to a first subject a quantity of a compound and a quantity of D-serine;
 (b) administering to a control subject a quantity of D-serine;
 (c) collecting a quantity of plasma from the first subject and plasma from the control subject at an interval after step (b) or step (c);
 (d) analyzing the quantity of D-serine in the plasma from the first subject by any one of the aforementioned methods; and
 (e) analyzing the quantity of D-serine in the plasma from the control subject by any one of the aforementioned methods.

In certain embodiments, the invention relates to a DAAO inhibitor identified by any one of the aforementioned methods.

In certain embodiments, the invention relates to a method of treating a mental disorder in a subject in need thereof comprising the step of co-administering to the subject a therapeutically effective amount of D-serine and a therapeutically effective amount a DAAO inhibitor identified by any one of the aforementioned methods.

BRIEF DESCRIPTION OF THE DRAWINGS

FIG. 1 shows extraction of D-serine from plasma by solid phase extraction (SPE) and subsequent determination of D-serine levels using the DAAO enzyme coupled assay.

FIG. 2 shows ex-vivo determination of plasma D-serine by the SPE/DAAO method after oral administration of D-serine±DAAO inhibitors–CD1 mice were given D-serine (326 µmoles/kg, po)±DAAO inhibitors CBIO (180 µmoles/kg) or TPC (160 µmoles/kg). Plasma was collected at 0.5, 1, 2, 3, and 6 hours after dosage. D-serine was extracted from plasma by SPE and its levels determined by the DAAO reaction. FIG. 2(C) depicts D-serine±TPC. $IC_{50}$ values for CBIO (D. Ferraris, et al. J Med Chem 51 (2008) 3357-9) and TPC (S. M. Smith, et al. J Pharmacol Exp Ther 328 (2009) 921-30) were averaged from those listed in the literature. Each data point is the average of data from 3 separate mice; error bars correspond to ±S.E.M. D-serine standard curves were constructed for each experiment.

DETAILED DESCRIPTION

I. General

Described herein are assays that involve SPE isolation of D-serine from plasma followed by quantitation of D-serine using the DAAO-catalyzed reaction. In certain embodiments, the invention relates to a method of screening for compounds that exhibit DAAO inhibition.

Figure 1A:
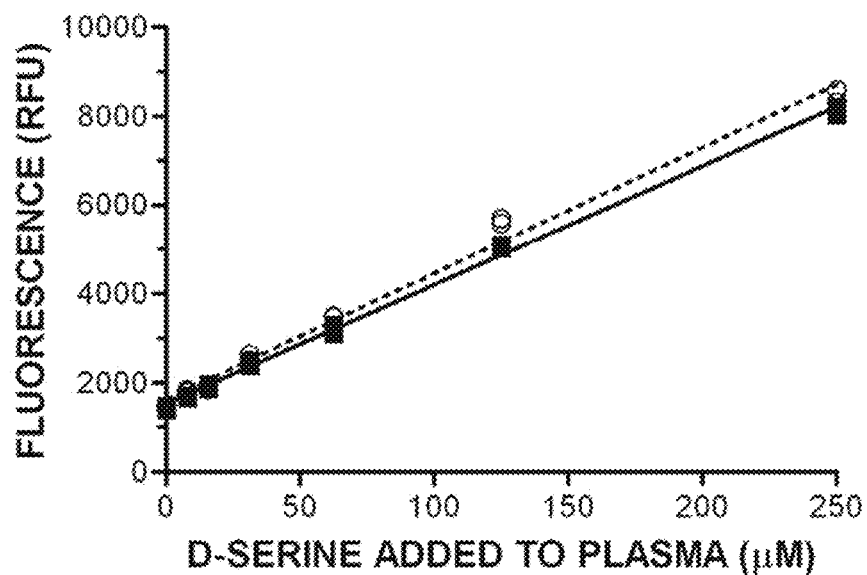
In FIG. 1(A), D-serine at various concentrations was added to plasma in the presence of 100 µM CBIO (filled squares, solid line) or 1% DMSO vehicle (empty circles, dashed line). D-serine was separated from CBIO by solid phase extraction. Subsequently, D-serine concentrations were determined using the DAAO-catalyzed conversion of D-serine to fluorescent resorufin in the DAAO enzyme coupled assay (materials and methods). Fluorescence readings (n=2) in relative fluorescent units (RFU) were obtained from end point measurements after the DAAO reaction was allowed to go completion. Single measurements are shown. A fluorescence (RFU) vs. D-serine (µM) standard curve was constructed with each experiment.
Figure 2A:
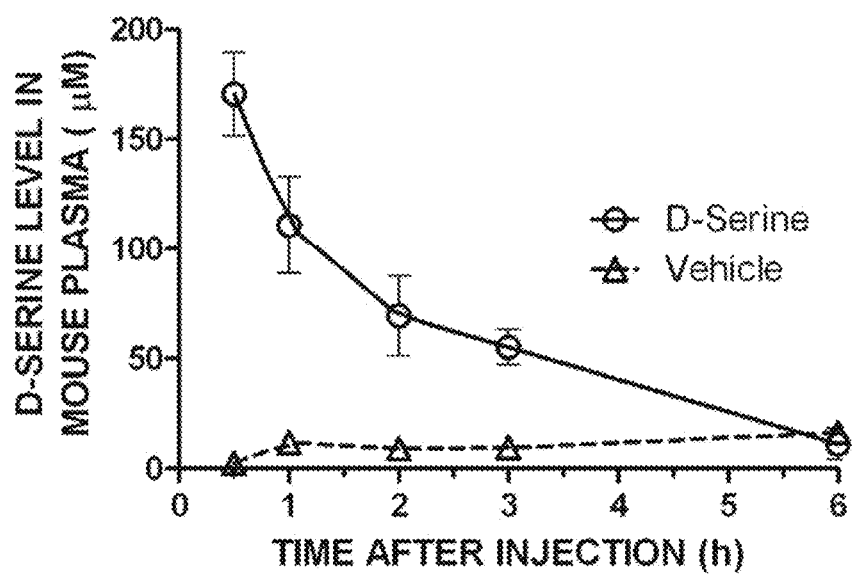
FIG. 2(A) depicts D-serine alone.
Figure 2B:
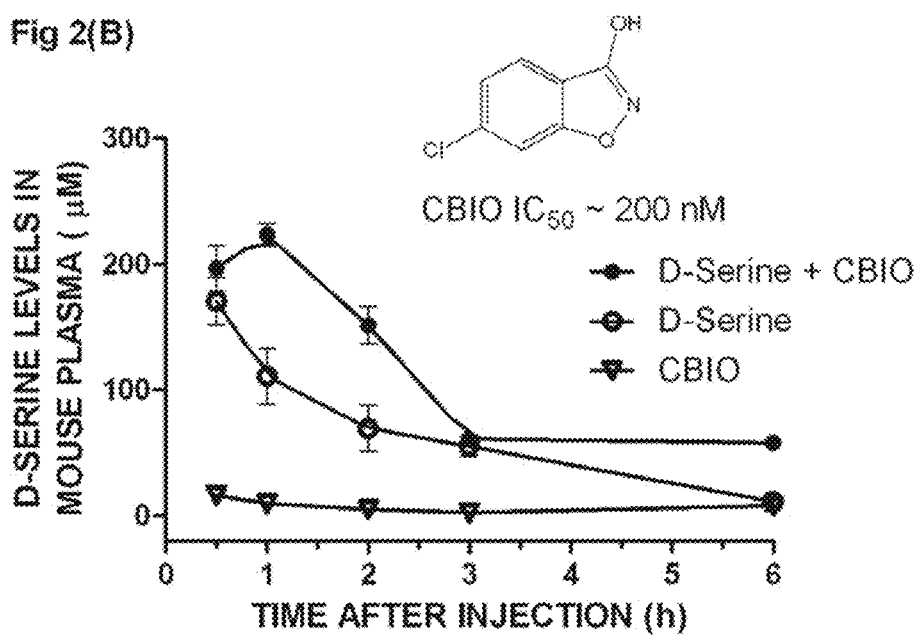
FIG. 2(B) depicts CBIO alone, D-serine±CBIO

D-serine concentrations were linear with fluorescence in the 4-250 µM (FIG. 1A), and well within the expected concentration ranges of plasma D-serine after D-serine administration (±) DAAO inhibitors (FIG. 2B and FIG. 2C). In certain embodiments, the method could be readily adapted to the determination of other exogenously added DAAO substrates such as D-alanine or D-proline, as well as to other biological matrices such as brain or peripheral tissues from different species. The new method offers substantial time savings over the traditional HPLC methods currently employed.

II. Definitions

In order that the present invention may be more readily understood, certain terms are first defined. Additional definitions are set forth throughout the detailed description.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

"Schizophrenia" refers to a mental disorder or group of mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays described herein. The term "small organic molecule" refers to a small molecule that is often identified as being an organic or medicinal compound, and does not include molecules that are exclusively nucleic acids, peptides or polypeptides.

As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human). In some embodiments, the subject or patient is afflicted with schizophrenia.

The phrases "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Abbreviations used include:
BID, (bis in die) twice a day;
CBIO, 5-chloro-benzo[d]isoxazol-3-ol;

DAAO, D-amino acid oxidase;
HPLC, High-performance liquid chromatography;
NBD-F, 4-fluoro-7-nitro-2,1,3-benzoxadiazole;
NMDA, N-methyl-D-aspartate;
ODS, octadecyl silane;
RFU, relative fluorescent units;
SPE, solid phase extraction;
TID, (ter in die) three times a day; and
TPC, 4H-thieno[3,2-b]pyrrole-5-carboxylic acid.

III. Solid-Phase Extraction

Solid-phase extraction (SPE) is a separation process by which compounds that are dissolved or suspended in a liquid mixture are separated from other compounds in the mixture according to their physical and chemical properties. Solid phase extraction can be used to isolate analytes of interest from a wide variety of matrices, including urine, blood, water, beverages, soil, and animal tissue.

SPE uses the affinity of solutes dissolved or suspended in a liquid ("mobile phase") for a solid through which the sample is passed ("stationary phase") to separate a mixture into desired and undesired components. In certain embodiments, the desired analyte of interest in the sample is retained on the stationary phase. The portion that passes through the stationary phase is discarded because it contains undesired impurities. The portion retained on the stationary phase can then be removed from the stationary phase for collection in an additional step, in which the stationary phase is rinsed with an appropriate eluent.

The stationary phase comes in the form of a packed syringe-shaped cartridge, a 96-well plate, a 47- or 90-mm flat disk, or a MEPS device, each of which can be mounted on its specific type of extraction manifold.

Ion exchange sorbents separate analytes based on electrostatic interactions between the analyte of interest and the positively charged groups on the stationary phase. For ion exchange to occur, both the stationary phase and sample must be at a pH where both are charged.

For example, cation exchange sorbents are derivatized with functional groups that interact and retain positively charged cations, such as bases. Strong cation exchange sorbents contain aliphatic sulfonic acid groups that are always negatively charged in aqueous solution. To elute the analyte from either the strong sorbent, the stationary phase is washed with a solvent that neutralizes ionic interaction between the analyte and the stationary phase.

IV. Exemplary Analytical Methods

In certain embodiments, the invention relates to a method of quantifying D-serine in plasma comprising the steps of:
(a) contacting a quantity of plasma with a quantity of a first acidic liquid, wherein the plasma comprises D-serine, thereby forming an acidified sample;
(b) contacting the acidified sample with a quantity of a cation exchange resin, thereby separating the acidified sample into a first component and a second component, wherein the first component comprises D-serine and is retained on the resin;
(c) rinsing the resin containing the retained first component with a quantity of a second acidic liquid;
(d) contacting the resin with a quantity of a first basic liquid, thereby eluting from the resin D-serine and forming a D-serine eluent;
(e) contacting the D-serine eluent with flavin adenine dinucleotide and a quantity of DAAO in the presence of Amplex Red and a quantity of horse radish peroxidase, thereby forming resorufin; and
(f) detecting a fluorescence signal from resorufin.

In certain embodiments, the invention relates to any one of the aforementioned methods, further comprising the step of:
(a') contacting a quantity of cation exchange resin with a quantity of a third acidic liquid.

In certain embodiments, the invention relates to any one of the aforementioned methods, wherein the pH of the third acidic liquid is from about 1.0 to about 2.0. In certain embodiments, the invention relates to any one of the aforementioned methods, wherein the pH of the third acidic liquid is about 1.0, about 1.1, about 1.2, about 1.3, about 1.4, about 1.5, about 1.6, about 1.7, about 1.8, about 1.9, or about 2.0.

In certain embodiments, the invention relates to any one of the aforementioned methods, wherein the third acidic liquid comprises HCl. In certain embodiments, the invention relates to any one of the aforementioned methods, wherein the third acidic liquid comprises HCl at a concentration of from about 0.015 N to about 0.045 N. In certain embodiments, the invention relates to any one of the aforementioned methods, wherein the third acidic liquid comprises HCl at a concentration of about 0.015 N, about 0.02 N, about 0.025 N, about 0.03 N, about 0.035 N, about 0.04 N, or about 0.045 N.

In certain embodiments, the invention relates to any one of the aforementioned methods, wherein the quantity of plasma is from about 20 µL to about 80 µL. In certain embodiments, the invention relates to any one of the aforementioned methods, wherein the quantity of plasma is from about 40 µL to about 60 µL. In certain embodiments, the invention relates to any one of the aforementioned methods, wherein the quantity of plasma is about 40 µL, about 45 µL, about 50 µL, about 55 µL, or about 60 µL.

In certain embodiments, the invention relates to any one of the aforementioned methods, wherein the pH of the first acidic liquid is from about 1.0 to about 2.0. In certain embodiments, the invention relates to any one of the aforementioned methods, wherein the pH of the first acidic liquid is about 1.0, about 1.1, about 1.2, about 1.3, about 1.4, about 1.5, about 1.6, about 1.7, about 1.8, about 1.9, or about 2.0.

In certain embodiments, the invention relates to any one of the aforementioned methods, wherein the first acidic liquid comprises HCl. In certain embodiments, the invention relates to any one of the aforementioned methods, wherein the first acidic liquid comprises HCl at a concentration of from about 0.015 N to about 0.045 N. In certain embodiments, the invention relates to any one of the aforementioned methods, wherein the first acidic liquid comprises HCl at a concentration of about 0.015 N, about 0.02 N, about 0.025 N, about 0.03 N, about 0.035 N, about 0.04 N, or about 0.045 N.

In certain embodiments, the invention relates to any one of the aforementioned methods, wherein the quantity of first acidic liquid is from about 125 µL to about 375 µL. In certain embodiments, the invention relates to any one of the aforementioned methods, wherein the quantity of first acidic liquid is from about 150 µL to about 350 µL. In certain embodiments, the invention relates to any one of the aforementioned methods, wherein the quantity of first acidic liquid is about 150 µL, about 160 µL, about 170 µL, about 180 µL, about 190 µL, about 200 µL, about 210 µL, about 220 µL, about 230 µL, about 240 µL, about 250 µL, about 260 µL, about 270 µL, about 280 µL, about 290 µL, about 300 µL, about 310 µL, about 320 µL, about 330 µL, about 340 µL, or about 350 µL.

In certain embodiments, the invention relates to any one of the aforementioned methods, wherein the quantity of cation exchange resin is from about 100 µL to about 300 µL. In certain embodiments, the invention relates to any one of the aforementioned methods, wherein the quantity of cation exchange resin is from about 150 µL to about 250 µL. In certain embodiments, the invention relates to any one of the aforementioned methods, wherein the quantity of cation exchange resin is about 150 µL, about 160 µL, about 170 µL, about 180 µL, about 190 µL, about 200 µL, about 210 µL, about 220 µL, about 230 µL, about 240 µL, or about 250 µL.

In certain embodiments, the invention relates to any one of the aforementioned methods, wherein step (b) takes place in deep well spin plates.

In certain embodiments, the invention relates to any one of the aforementioned methods, wherein the separation of the acidified sample into the first component and the second component is aided by centrifugation.

In certain embodiments, the invention relates to any one of the aforementioned methods, wherein the resin and the acidified sample are centrifuged for from about 1 min to about 3 min. In certain embodiments, the invention relates to any one of the aforementioned methods, wherein the resin and the acidified sample are centrifuged for about 1 min, about 1.5 min, about 2 min, about 2.5 min, or about 3 min.

In certain embodiments, the invention relates to any one of the aforementioned methods, wherein the resin and the acidified sample are centrifuged at from about 100×g to about 300×g. In certain embodiments, the invention relates to any one of the aforementioned methods, wherein the resin and the acidified sample are centrifuged at about 100×g, about 150×g, about 200×g, about 250×g, or about 300×g.

In certain embodiments, the invention relates to any one of the aforementioned methods, further comprising the step of:

(b') disposing of the second component.

In certain embodiments, the invention relates to any one of the aforementioned methods, wherein the second acidic liquid has a pH from about 1.0 to about 2.0. In certain embodiments, the invention relates to any one of the aforementioned methods, wherein the pH of the second acidic liquid is about 1.0, about 1.1, about 1.2, about 1.3, about 1.4, about 1.5, about 1.6, about 1.7, about 1.8, about 1.9, or about 2.0.

In certain embodiments, the invention relates to any one of the aforementioned methods, wherein the second acidic liquid comprises HCl. In certain embodiments, the invention relates to any one of the aforementioned methods, wherein the second acidic liquid comprises HCl at a concentration of from about 0.015 N to about 0.045 N. In certain embodiments, the invention relates to any one of the aforementioned methods, wherein the second acidic liquid comprises HCl at a concentration of about 0.015 N, about 0.02 N, about 0.025 N, about 0.03 N, about 0.035 N, about 0.04 N, or about 0.045 N.

In certain embodiments, the invention relates to any one of the aforementioned methods, wherein the quantity of second acidic liquid is from about 125 µL to about 375 µL. In certain embodiments, the invention relates to any one of the aforementioned methods, wherein the quantity of second acidic liquid is from about 150 µL to about 350 µL. In certain embodiments, the invention relates to any one of the aforementioned methods, wherein the quantity of second acidic liquid is about 150 µL, about 160 µL, about 170 µL, about 180 µL, about 190 µL, about 200 µL, about 210 µL, about 220 µL, about 230 µL, about 240 µL, about 250 µL, about 260 µL, about 270 µL, about 280 µL, about 290 µL, about 300 µL, about 310 µL, about 320 µL, about 330 µL, about 340 µL, or about 350 µL.

In certain embodiments, the invention relates to any one of the aforementioned methods, wherein step (c) is repeated. In certain embodiments, the invention relates to any one of the aforementioned methods, wherein step (c) is completed two times or three times.

In certain embodiments, the invention relates to any one of the aforementioned methods, further comprising the step of:

(c') rinsing the resin containing the first component with a second basic liquid.

In certain embodiments, the invention relates to any one of the aforementioned methods, wherein the second basic liquid has a pH from about 7.5 to about 9.5. In certain embodiments, the invention relates to any one of the aforementioned methods, wherein the second basic liquid has a pH of about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, or about 9.5.

In certain embodiments, the invention relates to any one of the aforementioned methods, wherein the second basic liquid comprises 2-amino-2-hydroxymethyl-propane-1,3-diol (Tris). In certain embodiments, the invention relates to any one of the aforementioned methods, wherein the second basic liquid comprises 2-amino-2-hydroxymethyl-propane-1,3-diol at a concentration of from about 50 mM to about 150 mM. In certain embodiments, the invention relates to any one of the aforementioned methods, wherein the second basic liquid comprises 2-amino-2-hydroxymethyl-propane-1,3-diol at a concentration of about 50 mM, about 60 mM, about 70 mM, about 80 mM, about 90 mM, about 100 mM, about 110 mM, about 120 mM, about 130 mM, about 140 mM, or about 150 mM.

In certain embodiments, the invention relates to any one of the aforementioned methods, wherein the quantity of second basic liquid is from about 125 µL to about 375 µL. In certain embodiments, the invention relates to any one of the aforementioned methods, wherein the quantity of second basic liquid is from about 150 µL to about 350 µL. In certain embodiments, the invention relates to any one of the aforementioned methods, wherein the quantity of second basic liquid is about 150 µL, about 160 µL, about 170 µL, about 180 µL, about 190 µL, about 200 µL, about 210 µL, about 220 µL, about 230 µL, about 240 µL, about 250 µL, about 260 µL, about 270 µL, about 280 µL, about 290 µL, about 300 µL, about 310 µL, about 320 µL, about 330 µL, about 340 µL, or about 350 µL.

In certain embodiments, the invention relates to any one of the aforementioned methods, wherein step (c') is repeated. In certain embodiments, the invention relates to any one of the aforementioned methods, wherein step (c') is completed two times, three times, or four times.

In certain embodiments, the invention relates to any one of the aforementioned methods, wherein the first basic liquid has a pH from about 12 to about 14. In certain embodiments, the invention relates to any one of the aforementioned methods, wherein the first basic liquid has a pH of about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, or about 14.0.

In certain embodiments, the invention relates to any one of the aforementioned methods, wherein the first basic liquid comprises 2-amino-2-hydroxymethyl-propane-1,3-diol (Tris). In certain embodiments, the invention relates to any one of the aforementioned methods, wherein the first basic liquid comprises 2-amino-2-hydroxymethyl-propane-1,3-diol at a concentration of from about 50 mM to about 150 mM. In certain embodiments, the invention relates to any one of the aforementioned methods, wherein the first basic liquid comprises 2-amino-2-hydroxymethyl-propane-1,3-diol at a concentration of about 50 mM, about 60 mM, about 70 mM, about 80 mM, about 90 mM, about 100 mM, about 110 mM, about 120 mM, about 130 mM, about 140 mM, or about 150 mM.

In certain embodiments, the invention relates to any one of the aforementioned methods, wherein the quantity of first basic liquid is from about 125 µL to about 375 µL. In certain embodiments, the invention relates to any one of the aforementioned methods, wherein the quantity of first basic liquid is from about 150 µL to about 350 µL. In certain embodiments, the invention relates to any one of the aforementioned methods, wherein the quantity of first basic liquid is about 150 µL, about 160 µL, about 170 µL, about 180 µL, about 190 µL, about 200 µL, about 210 µL, about 220 µL, about 230 µL, about 240 µL, about 250 µL, about 260 µL, about 270 µL, about 280 µL, about 290 µL, about 300 µL, about 310 µL, about 320 µL, about 330 µL, about 340 µL, or about 350 µL.

In certain embodiments, the invention relates to any one of the aforementioned methods, wherein step (d) is repeated. In certain embodiments, the invention relates to any one of the aforementioned methods, wherein step (d) is completed two times or three times.

In certain embodiments, the invention relates to any one of the aforementioned methods, wherein step (e) is carried out in a buffered solution. In certain embodiments, the invention relates to any one of the aforementioned methods, wherein the buffered solution comprises Tris. In certain embodiments, the invention relates to any one of the aforementioned methods, wherein the buffered solution comprises Tris in a concentration of from about 50 mM to about 150 mM. In certain embodiments, the invention relates to any one of the aforementioned methods, wherein the buffered solution comprises Tris at a concentration of about 50 mM, about 60 mM, about 70 mM, about 80 mM, about 90 mM, about 100 mM, about 110 mM, about 120 mM, about 130 mM, about 140 mM, or about 150 mM.

In certain embodiments, the invention relates to any one of the aforementioned methods, wherein the pH of the buffered solution is from about 7.5 to about 9.5. In certain embodiments, the invention relates to any one of the aforementioned methods, wherein the pH of the buffered solution is about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, or about 9.5.

In certain embodiments, the invention relates to any one of the aforementioned methods, wherein the buffered solution comprises flavin adenine dinucleotide at a concentration of from about 5 µM to about 15 µM. In certain embodiments, the invention relates to any one of the aforementioned methods, wherein the buffered solution comprises flavin adenine dinucleotide at a concentration of about 5 µM, about 6 µM, about 7 µM, about 8 µM, about 9 µM, about 10 µM, about 11 µM, about 12 µM, about 13 µM, about 14 µM, or about 15 µM.

In certain embodiments, the invention relates to any one of the aforementioned methods, wherein the DAAO is porcine DAAO.

In certain embodiments, the invention relates to any one of the aforementioned methods, wherein the quantity of DAAO in the buffered solution is from about 20 units/mg to about 50 units/mg. In certain embodiments, the invention relates to any one of the aforementioned methods, wherein the quantity of DAAO in the buffered solution is about 20 units/mg, about 25 units/mg, about 30 units/mg, about 35 units/mg, about 40 units/mg, about 45 units/mg, or about 50 units/mg.

In certain embodiments, the invention relates to any one of the aforementioned methods, wherein the concentration of horse radish peroxidase in the buffered solution is from about 0.005 mg/mL to about 0.015 mg/mL. In certain embodiments, the invention relates to any one of the aforementioned methods, wherein the concentration of horse radish peroxidase in the buffered solution is about 0.005 mg/mL, about 0.006 mg/mL, about 0.007 mg/mL, about 0.008 mg/mL, about 0.009 mg/mL, about 0.01 mg/mL, about 0.011 mg/mL, about 0.012 mg/mL, about 0.013 mg/mL, about 0.014 mg/mL, or about 0.015 mg/mL.

In certain embodiments, the invention relates to any one of the aforementioned methods, wherein the concentration of Amplex Red in the buffered solution is from about 25 µM to about 75 µM. In certain embodiments, the invention relates to any one of the aforementioned methods, wherein the concentration of Amplex Red in the buffered solution is about 25 µM, about 30 µM, about 35 µM, about 40 µM, about 45 µM, about 50 µM, about 55 µM, about 60 µM, about 65 µM, about 70 µM, or about 75 µM.

In certain embodiments, the invention relates to any one of the aforementioned methods, further comprising the step of (e') providing a light source, wherein the wavelength of the light source is about 530 nm.

In certain embodiments, the invention relates to any one of the aforementioned methods, wherein the fluorescence of resorufin is measured at about 590 nm.

In certain embodiments, the invention relates to any one of the aforementioned methods, wherein a fluorescence signal is detected at intervals for from about 30 min to about 90 min. In certain embodiments, the invention relates to any one of the aforementioned methods, wherein a fluorescence signal is detected at intervals for about 30 min, about 40 min, about 50 min, about 60 min, about 70 min, about 80 min, or about 90 min.

In certain embodiments, the invention relates to any one of the aforementioned methods, wherein the detection intervals are from about 2 min to about 8 min. In certain embodiments, the invention relates to any one of the aforementioned methods, wherein the detection intervals are about 2 min, about 3 min, about 4 min, about 5 min, about 6 min, about 7 min, or about 8 min.

V. Exemplary Screening Methods

In certain embodiments, the invention relates to a method of determining if a compound is a DAAO inhibitor, comprising the steps of (a) administering to a first subject a quantity of a compound and a quantity of D-serine;

(b) administering to a control subject a quantity of D-serine;

(c) collecting a quantity of plasma from the first subject and plasma from the control subject at an interval after step (b) or step (c);

(d) analyzing the quantity of D-serine in the plasma from the first subject by any one of the aforementioned methods; and (e) analyzing the quantity of D-serine in the plasma from the control subject by any one of the aforementioned methods.

In certain embodiments, the invention relates to any one of the aforementioned methods, further comprising step (f): comparing the quantity from step (d) to the quantity from step (e) and determining that the compound is a DAAO inhibitor if the quantity from step (d) is substantially larger than the quantity from step (e).

In certain embodiments, the invention relates to any one of the aforementioned methods, wherein the quantity of D-serine is from about 150 μmoles/kg to about 450 μmoles/kg. In certain embodiments, the invention relates to any one of the aforementioned methods, wherein the quantity of D-serine is about 150 μmoles/kg, about 175 μmoles/kg, about 200 μmoles/kg, about 225 μmoles/kg, about 250 μmoles/kg, about 275 μmoles/kg, about 300 μmoles/kg, about 325 μmoles/kg, about 350 μmoles/kg, about 375 μmoles/kg, about 400 μmoles/kg, about 425 μmoles/kg, or about 450 μmoles/kg.

In certain embodiments, the invention relates to any one of the aforementioned methods, wherein the D-serine is administered orally.

In certain embodiments, the invention relates to any one of the aforementioned methods, wherein the compound is a small molecule.

In certain embodiments, the invention relates to any one of the aforementioned methods, wherein the quantity of compound is from about 75 μmoles/kg to about 450 μmoles/kg. In certain embodiments, the invention relates to any one of the aforementioned methods, wherein the quantity of compound is about 75 μmoles/kg, about 100 μmoles/kg, about 125 μmoles/kg, about 150 μmoles/kg, about 175 μmoles/kg, about 200 μmoles/kg, about 225 μmoles/kg, about 250 μmoles/kg, about 275 μmoles/kg, about 300 μmoles/kg, about 325 μmoles/kg, about 350 μmoles/kg, about 375 μmoles/kg, about 400 μmoles/kg, about 425 μmoles/kg, or about 450 μmoles/kg.

In certain embodiments, the invention relates to any one of the aforementioned methods, wherein the compound is administered orally.

In certain embodiments, the invention relates to any one of the aforementioned methods, wherein the interval after step (b) or step (c) is about 0.25 h, about 0.5 h, about 1 h, about 2 h, about 3 h, about 4 h, about 5 h, about 6 h, about 7 h, about 8 h, or about 9 h.

In certain embodiments, the invention relates to any one of the aforementioned methods, wherein the quantity of plasma is from about 20 μL to about 80 μL. In certain embodiments, the invention relates to any one of the aforementioned methods, wherein the quantity of plasma is from about 40 μL to about 60 μL. In certain embodiments, the invention relates to any one of the aforementioned methods, wherein the quantity of plasma is about 40 μL, about 45 μL, about 50 μL, about 55 μL, or about 60 μL.

In certain embodiments, the invention relates to any one of the aforementioned methods, wherein the first subject is a mammal. In certain embodiments, the invention relates to any one of the aforementioned methods, wherein the first subject is a mouse. In certain embodiments, the invention relates to any one of the aforementioned methods, wherein the first subject is a CD1 mouse.

In certain embodiments, the invention relates to any one of the aforementioned methods, wherein the control subject is a mammal. In certain embodiments, the invention relates to any one of the aforementioned methods, wherein the control subject is a mouse. In certain embodiments, the invention relates to any one of the aforementioned methods, wherein the control subject is a CD1 mouse.

VI. Exemplary DAAO Inhibitors

In certain embodiments, the invention relates to a DAAO inhibitor identified by any one of the aforementioned methods.

In certain embodiments, the invention relates to any one of the aforementioned DAAO inhibitors, wherein the DAAO inhibitor has an $IC_{50}$ from about 1 nM to about 300 nM. In certain embodiments, the invention relates to any one of the aforementioned DAAO inhibitors, wherein the DAAO inhibitor has an $IC_{50}$ from about 10 nM to about 200 nM. In certain embodiments, the invention relates to any one of the aforementioned DAAO inhibitors, wherein the DAAO inhibitor has an $IC_{50}$ of about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, or about 200 nM.

In certain embodiments, the invention relates to any one of the aforementioned DAAO inhibitors, wherein the DAAO inhibitor is not positively charged at pH from about 1.0 to about 2.0. In certain embodiments, the invention relates to any one of the aforementioned DAAO inhibitors, wherein the DAAO inhibitor is not positively charged at pH about 1.0, about 1.1, about 1.2, about 1.3, about 1.4, about 1.5, about 1.6, about 1.7, about 1.8, about 1.9, or about 2.0.

VII. Exemplary Methods of Treatment

In certain embodiments, the invention relates to a method of treating a mental disorder in a subject in need thereof comprising the step of co-administering to the subject a therapeutically effective amount of D-serine and a therapeutically effective amount of any one of the aforementioned DAAO inhibitors.

In certain embodiments, the invention relates to any one of the aforementioned methods, wherein the mental disorder is schizophrenia.

DAAO inhibitors may be administered by any means known to one of ordinary skill in the art. For example, the inventive compounds may be administered orally, parenterally, by inhalation spray, topically, rectally, nasally, buccally, vaginally, or via an implanted reservoir. The term "parenteral" as used herein includes subcutaneous, intravenous, intramuscular, intraperitoneal, intrathecal, intraventricular, intrasternal, intracranial, and intraosseous injection and infusion techniques. The exact administration protocol will vary depending upon various factors including the age, body weight, general health, sex and diet of the patient; the determination of specific administration procedures would be routine to an one of ordinary skill in the art.

The inventive compounds may be administered by a single dose, multiple discrete doses or continuous infusion. Pump means, particularly subcutaneous pump means, are useful for continuous infusion.

Dose levels on the order of about 0.001 mg/kg/d to about 10,000 mg/kg/d of an inventive compound are useful for the inventive methods. In one embodiment, the dose level is about 0.1 mg/kg/d to about 1,000 mg/kg/d. In another embodiment, the dose level is about 1 mg/kg/d to about 100 mg/kg/d. The specific dose level for any particular patient will vary depending upon various factors, including the activity and the possible toxicity of the specific compound employed; the age, body weight, general health, sex and diet of the patient; the time of administration; the rate of excretion; the drug combination; the severity of the congestive heart failure; and the form of administration. Typically, in vitro dosage-effect results provide useful guidance on the proper doses for patient administration. Studies in animal models are also helpful.

The considerations for determining the proper dose levels are well known in the art and within the skills of an ordinary physician.

Any known administration regimen for regulating the timing and sequence of drug delivery may be used and repeated as necessary to effect treatment in the inventive methods. The regimen may include pretreatment and/or co-administration with additional therapeutic agent(s).

The inventive compounds can be administered alone or in combination with one or more additional therapeutic agent(s) for simultaneous, separate, or sequential use. The inventive compounds may be co-administered with one or more additional therapeutic agent(s) either (i) together in a single formulation, or (ii) separately in individual formulations designed for optimal release rates of their respective active agent.

EXEMPLIFICATION

This invention is further illustrated by the following examples which should not be construed as limiting. The contents of all references, patents and published patent applications cited throughout this application, as well as the Figures, are incorporated herein by reference.

Example 1

General Materials and Methods

Chemicals—5-chloro-benzo[d]isoxazol-3-ol (CBIO) and 4H-thieno[3,2-b]pyrrole-5-carboxylic acid (TPC) were bought from Maybridge and Chembridge respectively.

Animals—CD1 mice (6-8 wk old, Sprague Dawley, Harlan) were dosed orally with D-serine (30 mg/kg)±compounds. Animals were sacrificed 0.5, 1, 2, 3 and 6 h after dosing and blood was collected by cardiac puncture bleeds. Plasma was prepared and frozen at −80° C. until use.

Cation Exchange SPE—D-serine was added to normal mouse plasma at different concentrations to generate a standard curve. Plasma (50 µL) containing D-serine or plasma from D-serine treated animals was diluted in 200 µL 0.03 N HCl (pH 1.5). Even though protein denaturation must have occurred to some extent at pH 1.5, we did not observe precipitation or turbidity. Acidified samples were then added to a cation exchange resin (BioRad AG 50W-X4, 200 µL resin equilibrated with 0.03 N HCl) in deep well spin plates (Harvard Apparatus). Minicolumns were centrifuged for 2 min at 200×g. The resin was washed twice with 250 µL 0.03 N HCl and 3 times with 250 µL 100 mM Tris, pH 8.5. D-serine was eluted with 2 times 250 µL 100 mM Tris, pH 13.

D-serine Measurement—An aliquot (50 µL) of the D-serine eluant from the cation exchange SPE was used as the source of D-serine in the DAAO catalyzed reaction. The DAAO assay is an enzyme coupled assay that was adapted from a procedure that has been reported previously (P. E. Brandish, et al. J Biomol Screen 11 (2006) 481-87). Briefly, the reaction is carried out in Tris buffer (pH 8.5, 100 mM) in the presence of flavin adenine dinucleotide (10 µM). The peroxide formed from the oxidation of D-serine in the presence of porcine DAAO (34 units/mg, Sigma) was made to react with horse radish peroxidase (0.01 mg/ml, Sigma) in the presence of Amplex Red (50 µM, Invitrogen) to make resorufin. Fluorescence of resorufin (ex/em 530/590) was monitored in a SpectraMax Gemini XS fluorimeter for 1 h at 5 min intervals. D-serine concentrations were determined by interpolation from the standard curve of fluorescence vs. D-serine concentration.

Example 2

Extraction from Plasma and Quantification of D-Serine

Figures 3, 4:
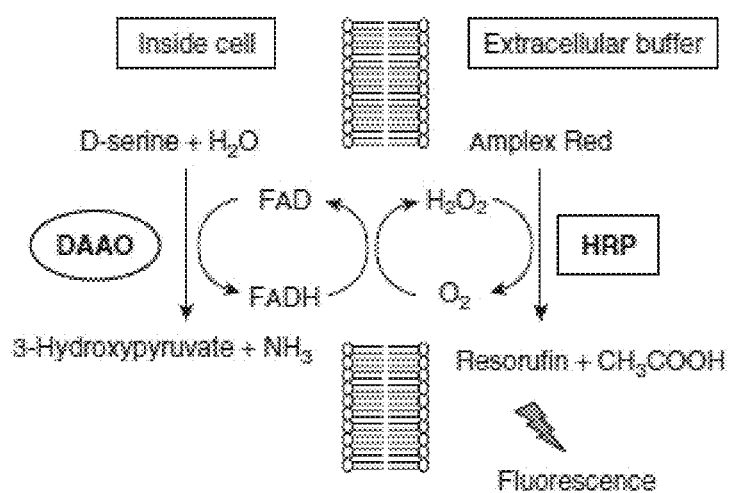
FIG. 3 tabulates binding and elution of D-serine from cation exchange resin. Mouse plasma was spiked with D-serine (50 µM) and applied to BioRad AG 50W-X4 cation exchange resin (2 mL wet volume) previously equilibrated at pH 1.5. Eluate fractions (2 mL) were collected and their pH measured. The pH of the eluate was then adjusted to 8.5 and the concentration of D-serine in the eluate was determined using the DAAO enzyme coupled assay.
FIG. 4 depicts the cell-based method on which the fluorescence assay of the invention is based. D-serine is oxidized by DAAO stably expressed in a Chinese hamster ovary (CHO) cell line. $H_2O_2$ is produced by the DAAO enzyme reaction and readily passes across the cell membrane. Horseradish peroxidase (HRP)/Amplex Red is used as an enzyme reporter system to quantify the amount of $H_2O_2$ produced by the DAAO enzyme reaction in which the signal is detected at an excitation of 544 nm and an emission of 590 nm.

The carboxylic acid of D-serine ($pK_a$ 2.1) is approximately 80% in the neutral form at pH 1.5 and the amino acid molecule acquires a net positive charge of 0.8 due to the protonated amine. When passed through a strong cation exchange column, positively charged D-serine binds to the resin while neutral molecules and acidic molecules do not bind and are removed through stepwise washes at higher pH values. The pH of the mobile phase was increased first to pH 8.5 and then to pH 13. The pH of the eluant changed gradually but D-serine eluted in a small volume between pH 2 and 9 immediately after the pH of the mobile phase was changed to pH 13 (FIG. 3).

Figure 1B:
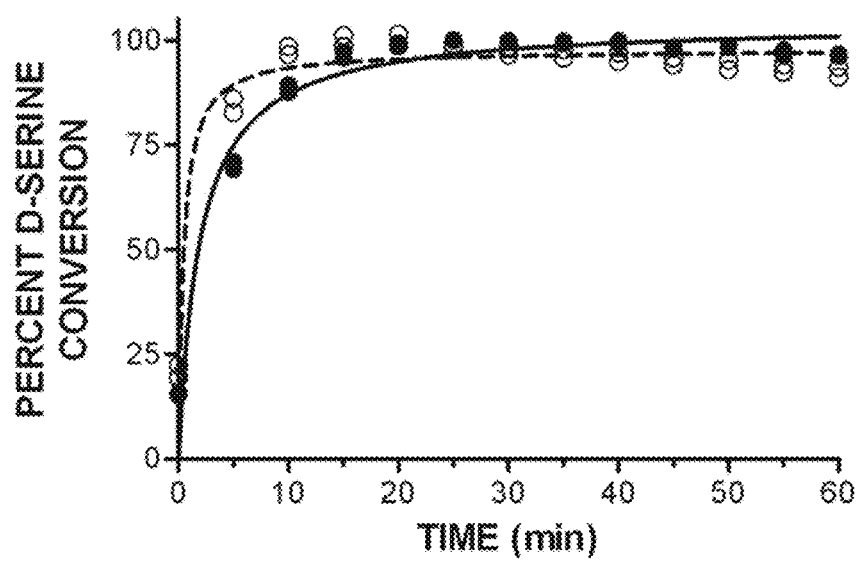
FIG. 1(B) depicts a kinetic trace of resorufin resulting from D-serine oxidation. D-serine (250 µM)±CBIO (100 µM) were added to plasma, and SPE/DAAO analysis was used to monitor D-serine concentrations at different time points during the DAAO-catalyzed oxidation. D-serine only: empty circles, dashed line. D-serine+CBIO: filled circles, solid line. Data points at each concentration are duplicates.

The eluant containing D-serine was then used as substrate in the DAAO catalyzed reaction. D-serine was the limiting reagent in the enzyme coupled reaction where a high concentration of DAAO was used. Plasma exhibited background fluorescence of about 1500 RFUs (FIG. 1A) possibly due to compounds that fluoresce and/or D-amino acids that are endogenously produced or of exogenous origin. The levels of several D-amino acids in mouse serum have been reported previously and they range from not detectable to 6 µM (A. Hashimoto, et al. Neurosci Lett 152 (1993) 33-36); these concentrations would give a low fluorescence background. Consequently, the higher background that is observed must come largely from other compounds that fluoresce that are not D-amino acids. In any case, background fluorescence was determined from control animals every time an experiment was carried out. This background was then subtracted from the plasma fluorescence obtained from animals that had been dosed with D-serine. Increasing concentrations of added D-serine in plasma that went through acidification, SPE and the DAAO-catalyzed reaction gave increasing fluorescence in a linear fashion in the 4-250 µM range (FIG. 1A). Fluorescence was then correlated to the concentrations of D-serine added to plasma to generate a standard curve, which was subsequently used to determine unknown concentrations of D-serine in plasma by interpolation. Since DAAO is specific for the D-isomer of serine, no separation of L and D enantiomers was necessary. It is important to note that the SPE/DAAO procedure works effectively only when the DAAO inhibitor does not carry positive charges at pH 1.5; this is the case with known DAAO inhibitors including CBIO. If a DAAO inhibitor present in plasma were to co-elute with D-serine during the SPE step, it would inhibit DAAO in the second step and compromise the determination of D-serine concentrations. In fact, during earlier experiments when using methanol instead of SPE to extract D-serine from plasma, D-serine did not separate from DAAO inhibitors which were found to inhibit DAAO in the second step of the procedure (data not shown). Consequently, it will be important to demonstrate that any DAAO inhibitor being evaluated using this assay does not co-elute with D-serine during SPE. When CBIO, a prototype DAAO inhibitor, was added to plasma at 100 µM (about 10.000-fold $K_i$) with D-serine and the samples were subsequently subjected to SPE/DAAO analysis, values obtained for D-serine were identical to those from samples that had not been spiked with DAAO inhibitor (FIG. 1A). The results are in accordance with the expectation that cation exchange resins do not bind to compounds without a positive charge. The above results were obtained from endpoint measurements of fluorescence after 1 h incubation when all D-serine was expected to have been oxidized. In order to ensure that the reaction had indeed reached an equilibrium stage, SPE/DAAO analyses were carried out at various time points. The reaction was complete within the first 15 min of incubation (FIG. 1B). Further, the rate of oxidation of D-serine obtained from plasma samples without CBIO was the same as that of D-serine from samples with CBIO added and subsequently removed by SPE. In a control experiment, when CBIO was not removed by SPE, oxidation of D-serine was completely inhibited (data not shown). The results indicated that 1 h incubation was more than sufficient for the DAAO reaction to reach equilibrium and that SPE removed CBIO from D-serine. There was a slight gradual decrease in the fluorescence at 40-60 min (FIG. 1B) possibly due to resorufin degradation so fluorescence measurements are best carried out at 20-30 min.

Resin and samples can be loaded into a 96-well plate and processed concomitantly within 2 h. A comparable analysis of 96 samples in sequential HPLC assays would take approximately 3 days assuming non-stop use of the instrument.

Example 3

Monitoring of Plasma D-Serine Levels Ex-Vivo

Mice were given D-serine (326 μmoles/kg, po) and their plasma collected at 0.5, 1, 2, 3, and 6 h after dosing. An aliquot (50 μL) of each plasma sample was subjected to SPE/DAAO to determine D-serine levels. The first time point at 0.5 h showed the highest D-serine plasma concentration; the maximum time of drug concentration ($T_{max}$) was likely reached at an earlier time point. The concentration of D-serine gradually decreased to the lowest concentration at 6 h (FIG. 2A). The estimated half-life of D-serine in mouse plasma was approximately 50 min. D-serine levels were the same as background levels when CBIO was administered in the absence of D-serine suggesting that the effect of DAAO inhibitors on plasma D-serine if any, would be largely on D-serine of exogenous origin.

When dosing D-serine (326 μmole/kg po) plus CBIO (180 μmoles/kg, po), the D-serine curve showed a similar maximum concentration to that observed when using D-serine alone but the overall curve was shifted to the right confirming that co-administration of a DAAO inhibitor increases exposure to D-serine (FIG. 2B). The shape of the curves and the timing and concentrations reached were similar to those previously reported using the HPLC methodology to determine plasma D-serine levels. D. Ferraris, et al. J Med Chem 51 (2008) 3357-59. Another DAAO inhibitor, 4H-thieno[3,2-b]pyrrole-5-carboxylic acid (TPC), was also dosed (160 μmoles/kg, po) with D-serine and assayed by SPE/DAAO. TPC also showed that the presence of the inhibitor in vivo shifted the exposure of D-serine in plasma (FIG. 2C).

The SPE/DAAO assay is currently being used in our laboratory to evaluate the effect of newly synthesized DAAO inhibitors on D-serine levels in plasma after oral co-administration with D-serine.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of quantifying D-serine in plasma comprising the steps of:
    (a) contacting a quantity of plasma with a quantity of a first acidic liquid, wherein the plasma comprises D-serine, thereby forming an acidified sample;
    (b) contacting the acidified sample with a quantity of a cation exchange resin, thereby separating the acidified sample into a first component and a second component, wherein the first component comprises D-serine and is retained on the resin;
    (c) rinsing the resin containing the retained first component with a quantity of a second acidic liquid;
    (d) contacting the resin with a quantity of a first basic liquid, thereby eluting from the resin D-serine and forming a D-serine eluent;
    (e) contacting the D-serine eluent with flavin adenine dinucleotide and a quantity of D-amino acid oxidase in the presence of a precursor to a fluorescence signal and a quantity of horse radish peroxidase; and
    (f) detecting the fluorescence signal.

2. The method of claim 1, wherein the quantity of plasma is from about 20 μL to about 80 μL.

3. The method of claim 1, wherein the pH of the first acidic liquid is from about 1.0 to about 2.0.

4. The method of claim 1, wherein the pH of second acidic liquid is from about 1.0 to about 2.0.

5. The method of claim 1, further comprising, after step (c) and prior to step (d), the step of:
    (c') rinsing the resin containing the first component with a second basic liquid, wherein the second basic liquid has a pH from about 7.5 to about 9.5.

6. The method of claim 1, wherein the first basic liquid has a pH from about 12 to about 14.

7. The method of claim 1, wherein step (e) is carried out in a buffered solution.

8. The method of claim 7, wherein the quantity of D-amino acid oxidase in the buffered solution is from about 20 units/mg to about 50 units/mg.

9. The method of claim 1, further comprising, after step (e) and prior to step (f), the step of
    (e') providing a light source, wherein the wavelength of the light source is about 530 nm.

10. The method of claim 1, wherein the precursor is Amplex Red.

* * * * *